United States Patent
Govari et al.

(10) Patent No.: US 12,023,092 B2
(45) Date of Patent: Jul. 2, 2024

(54) GUIDEWIRE WITH HEAVY INSULATION FOR USE DURING IRREVERSIBLE ELECTROPORATION (IRE)

(71) Applicant: Biosense Webster (Israel) Ltd., Yokneam (IL)

(72) Inventors: Assaf Govari, Haifa (IL); Andres Claudio Altmann, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 211 days.

(21) Appl. No.: 17/146,361

(22) Filed: Jan. 11, 2021

(65) Prior Publication Data

US 2022/0218410 A1   Jul. 14, 2022

(51) Int. Cl.
*A61B 18/14* (2006.01)
*A61B 18/00* (2006.01)

(52) U.S. Cl.
CPC ............ *A61B 18/1492* (2013.01); *A61B 2018/00083* (2013.01); *A61B 2018/00613* (2013.01); *A61B 2018/144* (2013.01)

(58) Field of Classification Search
CPC ........ A61B 18/1492; A61B 2018/0083; A61B 2018/144; A61B 2018/00577; A61B 2018/00601; A61B 2018/00791; A61B 2018/00642; A61B 2018/00875; A61B 2018/00589; A61B 2018/00839; A61B 2018/00023; A61B 2018/00351; A61B 2018/00595; A61B 2018/0063; A61B 2018/000178; A61B 2018/00982
See application file for complete search history.

(56) References Cited

U.S. PATENT DOCUMENTS

| 8,456,182 B2 | 6/2013 | Bar-Tal et al. |
| 2013/0030425 A1* | 1/2013 | Stewart .................. A61B 18/02 606/41 |
| 2013/0090647 A1 | 4/2013 | Smith |
| 2020/0261720 A1* | 8/2020 | Danitz ............... A61B 18/1206 |

FOREIGN PATENT DOCUMENTS

| EP | 2014329 A1 | 1/2009 | |
| EP | 2228094 A1 * | 9/2010 | ............. A61L 31/10 |
| EP | 2311518 A1 * | 4/2011 | ........... A61L 29/085 |
| EP | 2311518 A1 | 4/2011 | |
| WO | 2009/085798 A1 | 7/2009 | |
| WO | 2016/064753 A1 | 4/2016 | |

OTHER PUBLICATIONS

Extended European Search Reported dated Jun. 23, 2022, from corresponding application No. 22150737.9.

* cited by examiner

*Primary Examiner* — Linda C Dvorak
*Assistant Examiner* — Abigail Bock
(74) *Attorney, Agent, or Firm* — Troutman Pepper Hamilton Sanders LLP

(57) ABSTRACT

A guidewire includes a metal wire, a first electrically-insulating layer, and a second electrically-insulating layer. The metal wire has a distal end. The first electrically-insulating layer covers the wire. The second electrically-insulating layer covers the distal end of the guidewire, wherein a breakdown voltage of the second electrically-insulating layer is larger than that of the first electrically-insulating layer.

8 Claims, 2 Drawing Sheets

GUIDEWIRE WITH HEAVY INSULATION FOR USE DURING IRREVERSIBLE ELECTROPORATION (IRE)

FIELD OF THE INVENTION

The present invention relates generally medical probes, and specifically to electrically insulated cardiac probes.

BACKGROUND OF THE INVENTION

Electrical insulation on medical probes has been previously proposed in the patent literature. For example, PCT International Publication WO 2016/064753 describes segmented metallic guidewires that are suitable for MRI catheterization. Disclosed guidewires comprise a plurality of short conductive metallic segments that individually are short enough such that they do not resonate during MRI. The conductive segments are electrically insulated from each other and mechanically coupled together end-to-end via connectors, such as stiffness matched connectors, to provide a sufficiently long, strong, and flexible guidewire for catheterization that is non-resonant during MRI.

As another example, U.S. Patent Application Publication 2013/0090647 describes an ablation catheter configured to be navigated through a vessel to ablate tissue, the ablation catheter comprising an elongate catheter shaft having a proximal end and a distal end. An electrode is positioned near the distal end of the elongate shaft, and is configured to transmit radio-frequency energy into a vessel wall. An electrically insulative tip at the distal end of the catheter keeps the electrode away from the blood vessel wall.

SUMMARY OF THE INVENTION

An embodiment of the present invention provides a guidewire including a metal wire, a first electrically-insulating layer, and a second electrically-insulating layer. The metal wire has a distal end. The first electrically-insulating layer covers the wire. The second electrically-insulating layer covers the distal end of the guidewire, wherein a breakdown voltage of the second electrically-insulating layer is larger than that of the first electrically-insulating layer.

In some embodiments, a combined breakdown voltage of the first and second electrically-insulating layers is higher than a predefined voltage used in irreversible electroporation (IRE).

In some embodiments, the guidewire further includes a medical device coupled at a distal edge of the guidewire. In other embodiments, the medical device is a surgical tool.

There is additionally provided, in accordance with another embodiment of the present invention, a method including inserting into a heart of a patient a guidewire, wherein the guidewire includes (a) a metal wire having a distal end, (b) a first electrically-insulating layer covering the wire, and (c) a second electrically-insulating layer, which covers the distal end of the guidewire, wherein a breakdown voltage of the second electrically-insulating layer is larger than that of the first electrically-insulating layer. An ablation catheter is inserted into the heart, in a vicinity of the distal end of the guidewire. Using the IRE catheter, IRE pulses are applied in vicinity of the distal end of the guidewire.

In some embodiments, the ablation catheter and the distal end of the guidewire are in physical contact.

In some embodiments, inserting the ablation catheter comprises guiding the IRE catheter over the guidewire.

In some embodiments, the ablation catheter is an irreversible electroporation (IRE) catheter.

There is further provided, in accordance with another embodiment of the present invention, a manufacturing method including providing a metal wire having a distal end. The wire is covered with a first electrically-insulating layer. The distal end of the guidewire is covered with a second electrically-insulating layer, wherein a breakdown voltage of the second electrically-insulating layer is larger than that of the first electrically-insulating layer.

The present invention will be more fully understood from the following detailed description of the embodiments thereof, taken together with the drawings in which:

DETAILED DESCRIPTION OF EMBODIMENTS

Overview

Figure 1:
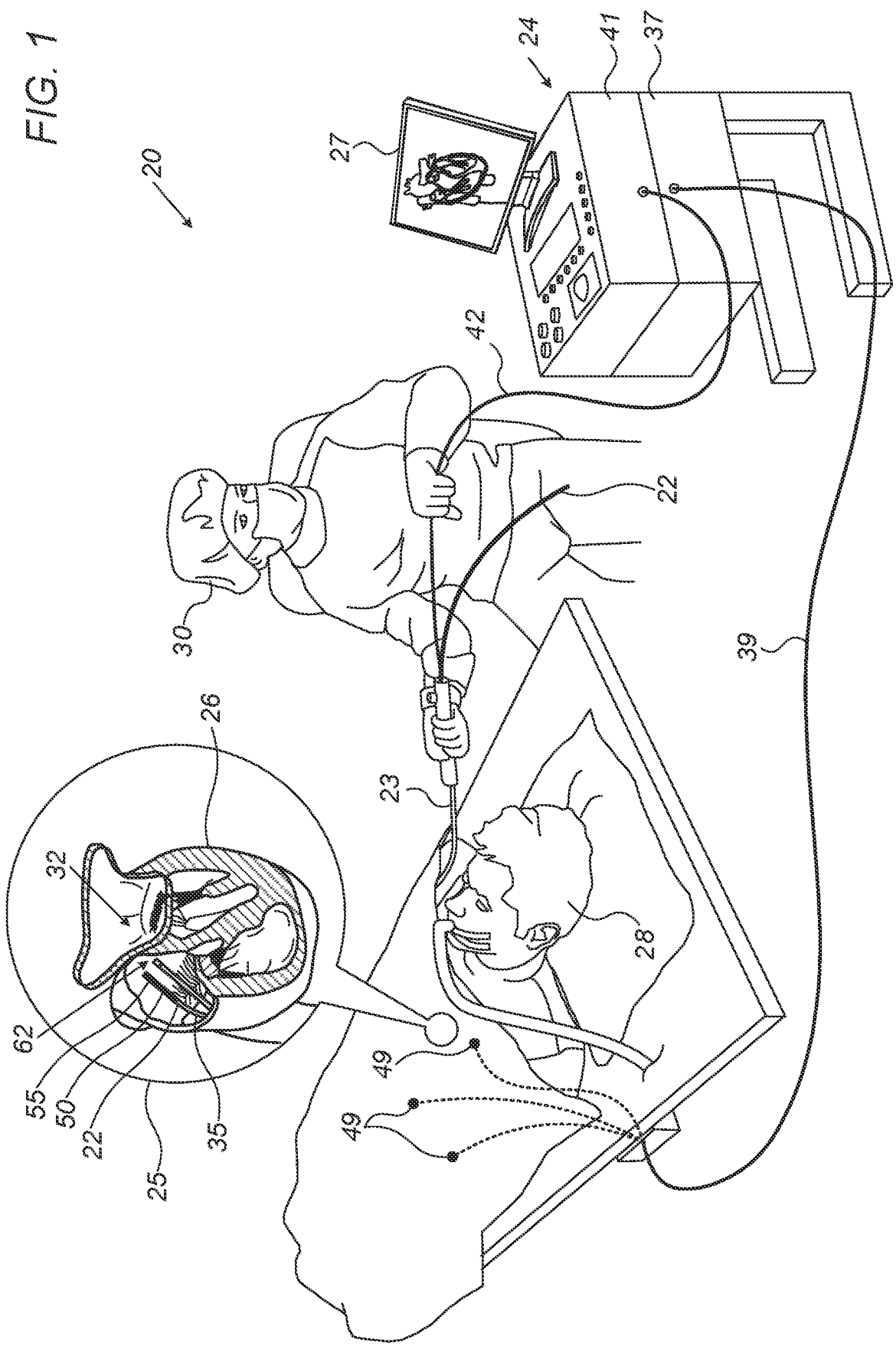
FIG. 1 is a schematic, pictorial illustration of a cardiac catheterization system comprising an irreversible electroporation (IRE) subsystem, in accordance with an embodiment of the present invention.

Guidewires used in invasive treatments of an internal organ, such as in cardiac surgery, are typically formed as long thin metal wires (e.g., of stainless steel and/or nitinol). In some cases, the guidewire may be formed as a wire coil. Such guidewires may be used to deploy, for example, a surgical tool or an implant. While guidewires may be electrically insulated, for example by being coated with Teflon, such insulation may not be able to withstand high voltages.

Some invasive procedures may further involve performing irreversible electroporation (IRE), also known as pulsed-field-ablation (PFA) at the treated location, such as may be performed during cardiac surgery. To this end an additional ablation catheter may be inserted into the organ. Such a catheter is fitted with one or more electrodes at its distal end that are used to apply IRE pulses with typical magnitudes of 2 kV or more. If a guidewire used during an IRE procedure comes into contact with an electrode delivering the IRE pulses, it poses a risk of electrocution to the operator holding the guidewire.

Embodiments of the present invention that are described hereinafter provide guidewires with additional electrical insulation over their distal end, for example over the distal-most 15 cm of the guidewire. The insulation material and thickness are selected to withstand the high voltages used for the IRE or PFA.

In some embodiments, the disclosed electrically insulated guidewire is used to guide an IRE catheter into the pulmonary vein (PV). In such a procedure, the guidewire is inserted through a channel in the catheter (e.g., a balloon catheter) to the PV and the balloon catheter is advanced over the guidewire to the PV target for ablation. During this process, the guidewire might bend and touch the ablation electrodes of the catheter directly, or be in proximity to the high voltage pulsed field electrodes. When applying the ablation energy, some of the energy might pass through the guidewire to outside the body, reach the proximal end of the guidewire, and cause electrocution to a user. Insulating the guidewire as in the disclosed techniques eliminates this hazard. Another need for heavy insulation is to prevent discharging energy from a user touching the guidewire to the heart, and preventing any energized (e.g., metallic object) touching the proximal end of the guidewire from passing undesired energy to the heart.

In some embodiments, the guidewire comprises a first insulating layer covering the aforementioned metal wire, and a second insulating layer, which covers the distal end of the guidewire, wherein the breakdown voltage of the second insulating layer is larger than that of the first insulating layer. The combined breakdown voltage of the first and second insulating layer is higher than voltages used in IRE.

In some embodiments, one or both of the insulation layers are implemented, for example, by anodizing the guidewire. In some embodiments, the guidewire has a single layer of insulation over an entire length that inserted into a human body, that can be of uniform thickness or of non-uniform thickness. Such insulation prevents, for example, unintentionally conducting an electrical pulse to an unspecified tissue location in the body. In some embodiments, the guidewire itself is made of an electrically non-conductive material, obviating the need for additional insulation layers.

By providing heavily insulated guidewires, a medical invasive procedure using IRE can be made safer.

System Description

FIG. 1 is a schematic, pictorial illustration of a cardiac catheterization system 20 comprising an irreversible electroporation (IRE) subsystem, in accordance with an embodiment of the present invention. System 20 is used for invasive cardiac treatments that involve using an IRE catheter 32 and a guidewire 22 (both seen in an inset 25). As seen, IRE catheter 32 incorporates electrodes 62 that are configured to apply high voltage (e.g. 2 kV) IRE pulses to ablate cardiac tissue. Guidewire 22 has a metal wire at its core (the wire shown in FIG. 2) that is covered with a first electrical insulation layer 35. Guidewire 22 has a distal end 50 that is further covered with heavy electrical insulation layer 55. The guidewire can be used for various applications, such as for carrying an invasive surgical tool or an implant.

Guidewire 22 is inserted through a sheath 23 into a heart 26. Physician 30 navigates guidewire 22 to a target location inside heart 26 by manipulating the guidewire using a manipulator near the proximal end of the guidewire and/or deflection from sheath 23.

In the shown embodiment, IRE catheter 32 is also inserted into the heart, using a shaft 42, with electrodes 62 of IRE catheter 32 being located in proximity to distal end 50 of the guidewire. IRE electrodes 62 are connected by wires running through shaft 42 to driver circuitry in a console 24.

Console 24 comprises a processor 41, typically a general-purpose computer, with suitable front end and electrical interface circuits 37 for receiving electrical position signals from patches 49. Processor 41 is connected to patches 49, which are attached to the chest skin of patient 26, by wires running through a cable 39. Console 24 drives a display 27, which shows the catheter 32 position inside heart 26.

A method of catheter position sensing using system 20 is implemented in various medical applications, for example in the CARTO™ system produced by Biosense Webster, which is described in detail in U.S. Pat. No. 8,456,182 and whose disclosure is incorporated herein by reference.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

Guidewire with Heavy Insulation for Use During Ire

Figure 2:
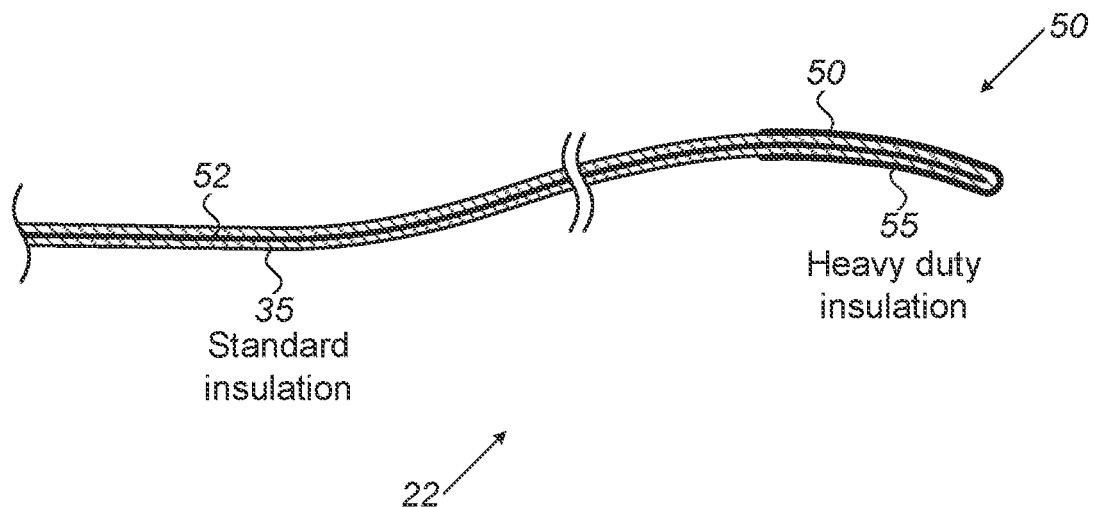
FIG. 2 is a schematic side view of a guidewire used with the system of FIG. 1, the guidewire comprising a heavy electrical insulation cover at its distal end, in accordance with an embodiment of the present invention.

FIG. 2 is a schematic side view of guidewire 22 used with system 20 of FIG. 1, the guidewire comprising a heavy electrical insulation cover 55 at its distal end 50, in accordance with an embodiment of the present invention.

As seen, guidewire 22, which is typically made of a metal wire 52, is covered with a first, standard electrical insulation layer 35. As seen, only distal end 50 is further covered with the heavy insulation layer 55.

Either the breakdown voltage of layer 55 alone, or combined with that of layer 35, is high enough to insulate wire 52 from an IRE voltage.

In example embodiments, the diameter of metal wire 52 is in the range of 1 micrometer to 500 micrometers. Insulation layer 35 may be made, for example, from PTFE, Polyurethane, Polyamide, or no insulation used.

Insulation layer 35 may have a thickness in the range of 1 micrometer to 500 micrometers. Insulation layer 55 may be made, for example, from Ethylene Tetrafluoroethylene (ETFE), silicone rubber (SR), Perfluoro-alkoxy (PFA), fluorinated ethylene propylene (FEP), Thermoplastic elastomers (TPE), and may have a thickness in the range of 1 micrometer to 500 micrometers. The length of the section of guidewire covered with layer 55 may be, for example, in the range of 10 mm to 150 mm. All the above figures and materials are given purely by way of example. In alternative embodiments, any other suitable configurations can be use.

The guidewire described in FIG. 2 is highly simplified for the sake of conceptual clarity. For example, guidewire 22 may carry at its distal edge a diagnostic and/or surgical device, neither of which is shown.

Figure 3:
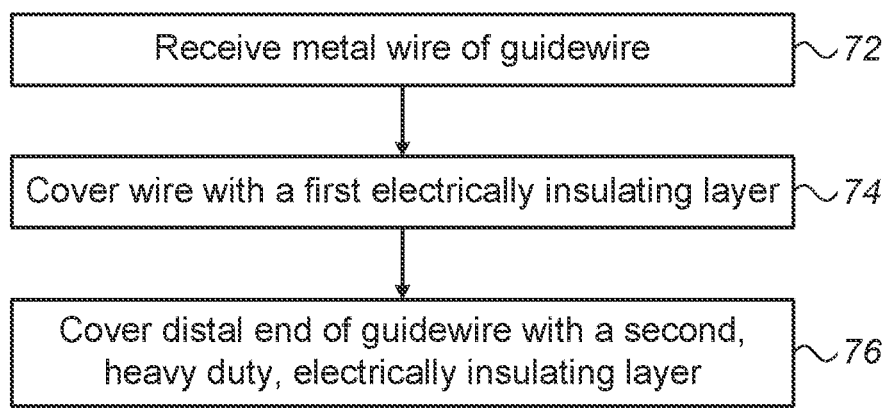
FIG. 3 is a flow chart that schematically illustrates a manufacturing method of the guidewire of FIG. 2, in accordance with an embodiment of the present invention.

FIG. 3 is a flow chart that schematically illustrates a manufacturing method of guidewire 22 of FIG. 2, in accordance with an embodiment of the present invention. The process begins with receiving a bare metal wire, such as wire 52, at a metal guidewire receiving step 72. Next, guidewire 22 is covered (e.g., coated) with a first layer of electrical insulating material such as Teflon, at a first insulation step 74.

At a second insulation step 76, a distal end 50 of guidewire 22 is further coated with heavy electrical insulation 55. Insulation material and thickness used for step 55 are chosen to electrically isolate the metal guidewire from very high voltages (e.g., of 2 kV). An example of layer 55 is an approximately 0.14 mm thick sleeve of Ethylene Tetrafluoroethylene (ETFE).

The example manufacturing method shown in FIG. 3 is chosen purely for the sake of conceptual clarity. Alternative or additional steps may be included (such as using epoxy), which have been omitted from the disclosure herein purposely in order to provide a more simplified flow chart. Although the embodiments described herein mainly address invasive cardiac procedures that involve IRE, the methods and systems described herein can also be used in other applications that require applying IRE, such as in neurology.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A guidewire, comprising:
a metal wire having a distal end;
a first electrically-insulating layer covering the wire including the distal end of the metal wire; and
a second electrically-insulating layer, which covers the distal end of the guidewire, wherein a breakdown voltage of the second electrically-insulating layer is larger than that of the first electrically-insulating layer, the first and second electrically-insulating layers each having a thickness in the range of 1 micrometer to 500 micrometers, and
the first and second electrically-insulating layers being stacked such that a combined breakdown voltage of the first and second electrically-insulating layers is at least 2 kilovolts.

2. The guidewire according to claim 1, further comprising a medical device coupled at a distal edge of the guidewire.

3. The guidewire according to claim 2, wherein the medical device is a surgical tool.

4. A method, comprising:
inserting into a heart of a patient a guidewire, wherein the guidewire comprises:
a metal wire having a distal end;
a first electrically-insulating layer covering the wire, which covers the distal end of the metal wire; and
a second electrically-insulating layer, which covers the distal end of the guidewire, wherein a breakdown voltage of the second electrically-insulating layer is larger than that of the first electrically-insulating layer, wherein the first and second electrically-insulating layers each have a thickness in the range of 1 micrometer to 500 micrometers, and wherein the first and second electrically-insulating layers are stacked such that a combined breakdown voltage of the first and second electrically-insulating layers is at least 2 kilovolts;
inserting into the heart an ablation catheter, in a vicinity of the distal end of the guidewire; and
using the ablation catheter, applying IRE pulses in vicinity of the distal end of the guidewire.

5. The method according to claim 4, wherein the ablation catheter and the distal end of the guidewire are in physical contact.

6. The method according to claim 4, wherein inserting the ablation catheter comprises guiding the ablation catheter over the guidewire.

7. The method according to claim 4, wherein the ablation catheter is an irreversible electroporation (IRE) catheter.

8. A manufacturing method, comprising:
providing a metal wire having a distal end;
covering the wire with a first electrically-insulating layer, including the distal end of the metal wire; and
covering the distal end of the guidewire with a second electrically-insulating layer, wherein a breakdown voltage of the second electrically-insulating layer is larger than that of the first electrically-insulating layer, wherein the first and second electrically-insulating layers each have a thickness in the range of 1 micrometer to 500 micrometers, and wherein the first and second electrically-insulating layers are stacked such that a combined breakdown voltage of the first and second electrically-insulating layers is at least 2 kilovolts.

* * * * *